United States Patent
Prater et al.

(10) Patent No.: US 9,134,341 B2
(45) Date of Patent: Sep. 15, 2015

(54) MULTIPLE MODULATION HETERODYNE INFRARED SPECTROSCOPY

(76) Inventors: Craig Prater, Santa Barbara, CA (US); Kevin Kjoller, Santa Barbara, CA (US)

(*) Notice: Subject to any disclaimer, the term of this patent is extended or adjusted under 35 U.S.C. 154(b) by 382 days.

(21) Appl. No.: 13/343,599

(22) Filed: Mar. 16, 2012

(65) Prior Publication Data
US 2012/0204296 A1    Aug. 9, 2012

(51) Int. Cl.
| | |
|---|---|
| G01Q 30/02 | (2010.01) |
| G01Q 60/34 | (2010.01) |
| G01N 21/3563 | (2014.01) |
| B82Y 35/00 | (2011.01) |
| G01N 21/17 | (2006.01) |

(52) U.S. Cl.
CPC .............. G01Q 60/34 (2013.01); B82Y 35/00 (2013.01); G01N 21/171 (2013.01); G01N 21/3563 (2013.01); G01Q 30/02 (2013.01)

(58) Field of Classification Search
CPC ....... G01Q 20/02; G01Q 30/02; G01Q 60/34; G01N 21/171
USPC .......................................... 73/105; 850/6, 33
See application file for complete search history.

(56) References Cited

U.S. PATENT DOCUMENTS

| | | | | |
|---|---|---|---|---|
| 5,003,815 | A * | 4/1991 | Martin et al. | 73/105 |
| 5,065,103 | A * | 11/1991 | Slinkman et al. | 324/458 |
| 5,267,471 | A * | 12/1993 | Abraham et al. | 73/105 |
| 5,955,660 | A * | 9/1999 | Honma | 73/105 |
| 6,085,580 | A * | 7/2000 | Ludeke et al. | 73/105 |
| 8,322,220 | B2 * | 12/2012 | Prater et al. | 73/606 |
| 8,387,443 | B2 * | 3/2013 | King et al. | 73/105 |
| 2005/0056782 | A1 * | 3/2005 | Shekhawat et al. | 250/306 |

OTHER PUBLICATIONS

Cuberes, M. T., "Intermittent-Contact Heterodyne Force Microscopy", Journal of Nanomaterials, vol. 2009, Article ID 762016, pp. 1-5.*

* cited by examiner

*Primary Examiner* — Daniel S Larkin
(74) *Attorney, Agent, or Firm* — Mark Rodgers (57) ABSTRACT

A heterodyne detection technique for highly localized IR spectroscopy based on an AFM. A pulsed IR source illuminates a sample and causes contact resonance of an AFM probe, which is a function of localized absorption. The probe is operated in intermittent contact mode and is therefore oscillated at a resonance frequency. A secondary oscillation is mixed in to the probe oscillation such that the sum of the secondary oscillation and the IR source pulse frequency is near another harmonic of the probe. A mixing effect causes measurable probe response at the other harmonic allowing data to be taken away from the pulse frequency.

21 Claims, 7 Drawing Sheets

Fig. 1

Prior Art

Fig. 2

Prior Art

MULTIPLE MODULATION HETERODYNE INFRARED SPECTROSCOPY

FEDERALLY SPONSORED RESEARCH

This invention was made with United States Government support under ATP Award 70NANB7H7025 awarded by the National Institute of Standards and Technology (NIST) and Award 0944400 awarded by the National Science Foundation. The United States Government has certain rights in the invention.

RELATED APPLICATIONS

Not Applicable

SEQUENCE LISTING

Not Applicable

BACKGROUND OF THE INVENTION

This invention is related to highly localized Infrared (IR) spectra on a sample surface utilizing an Atomic Force Microscope (AFM) and a variable wavelength modulated IR source, and specifically to a multiple frequency probe excitation technique leading to improved rejection of background effects and improved spatial resolution.

IR spectroscopy is a useful tool in many analytical fields, such as materials and life sciences. Conventional IR spectroscopy and microscopy, however, have resolution on the scale of many microns, limited by optical diffraction. It would be particularly useful to perform IR spectroscopy on a highly localized scale, on the order of biological organelles or smaller, at various points on a sample surface. Such a capability would provide information about the composition of the sample, such as location of different materials or molecular structures. Conventional infrared spectroscopy is a widely used technique to measure the characteristics of material. In many cases the unique signatures of IR spectra can be used to identify unknown material. Conventional IR spectroscopy is performed on bulk samples which gives compositional information but not structural information. Infrared microscopy allows collection of IR spectra with resolution on the scale of many microns resolution. Near-field scanning optical microscopy (NSOM) has been applied to some degree in infrared spectroscopy and imaging. Recently, a technique has been developed based on use of an AFM in a unique fashion to produce such localized spectra. This work was described in a publication entitled "Local Infrared Microspectroscopy with Sub-wavelength Spatial Resolution with an Atomic Force Microscope Tip Used as a Photo-thermal Sensor" Optics Letters, Vo. 30, No. 18, Sept.5, 2005. This technique is also described in detail in U.S. Pat. Nos. 8,001,830 and 8,402,819, commonly owned by the assignee of this invention, and whose contents are incorporated by reference. Those skilled in the art will comprehend the details of the technique in the publication and patent applications. The general technique is also referred to as Photo-Thermal Induced Resonance, or PTIR. It has also been called photothermal AFM-IR.

PTIR has been demonstrated in both research laboratories around the world and in commercial instrumentation developed by the assignee of this application. Although the spatial resolution obtained using this technique for IR spectroscopic identification of sample composition is superior to more conventional techniques, certain spatial resolution factors have been identified that might limit the technique for some applications. Specifically, the heating-produced interaction between the sample and the probe tip is not limited to the area directly under the apex of the probe tip. Both sample heating in the area around the tip and heating of the air under the cantilever contribute to the measured effect on the probe and act to delocalize the probe-sample interaction. Since the PTIR technique typically relies on a pulsed IR source, these background effects correlate with the pulse frequency, which in current PTIR set-ups also correlates to the data acquisition window.

Wickramasinghe (Image Force Microscopy of Molecular Resonance: A Microscopic Principle, Wikramasinghe et al, Applied Physics Letters 97, 073121, 2010), incorporated herein by reference, has recently showed the ability to obtain optical spectroscopic information in the visual spectrum with the tip of an AFM by using a heterodyne detection technique. Specifically, the cantilever was oscillated at a frequency $f_1$ close to the fundamental resonance of the cantilever $f_{c1}$. Visible laser light sources were modulated at a second frequency $f_m$ such that $f_1+f_m=f_{c2}$, where $f_{c2}$ is the second resonance mode of the cantilever. Effectively, this approach stimulates a non-linear mixing effect on the probe at $f_{c2}$. Wickramasinge attributed the nonlinear mixing to nonlinear tip-sample forces when the tip is very close to the sample in attractive "tapping" mode. Using this technique Wickramasinghe detected single molecules of a dye with strong absorption in the visible. Wickramasinghe also suggested that it should be possible to make similar measurements at other radiation frequencies, including infrared, but he did not address any specific practical implementations. For the IR case, the probe amplitude waveform will be a mix of the oscillation amplitude and the ringdown waveform due to IR pulses at frequency $f_m$, which may be from absorption or other effects such as mentioned by Wickramasinghe. Wickramasinghe in his visual spectrum setup selects $f_m$ to be such that the sum of $f_m$ and $f_{c1}$ is equal to $f_{c2}$ a second harmonic of the cantilever, and since $f_{c2}$ is a resonance, any interaction will be magnified and more easily detectable. Since the mixing effect is a sum/difference non-linear mixing taking place only when the tip is very near the sample, i.e. at the bottom of the "tapping" (intermittent contact or non-contact) oscillation, data taken at the sum or difference frequency, $(f_{c1}-f_m)$ and $(f_{c1}+f_m)=f_{c2}$ only includes interaction of the tip itself with the surface,. This has the effect that measurements made at $f_{c2}$ are not sensitive to effects that only have a component at $f_m$, the radiation modulation frequency, thereby rejecting the background effects which happen at $f_m$ and only including effects which have an $f_{c1}$ component, specifically the oscillating contact of the tip and sample. This has the effect of localizing the measurement.

In practice, Wickramasinghe's suggestion that the technique could be used in the IR is far from straightforward. Wickramasinghe used narrow band CW laser sources and the spectra he obtained only contained a few spectral data points, each requiring the use of a different laser. There are few broadly tunable sources in the infrared and even fewer that operate in CW mode. Even with such a source, Wickramasinghe teaches a technique that would require modulation of the light source at the difference frequency between a cantilever's first and second resonance. As will be described below, this is impractical in the IR. Cantilevers used in AC mode AFM typically have resonance frequencies in the range of 50 kHz to around 1 MHz or higher. The 2nd flexural resonant mode for a rectangular cantilever is roughly 6× higher in frequency, ranging then from 300 kHz to 6 MHz or higher. So an IR laser modulation frequency designed to excite $f_{c2}$ needs to be in the range of 250 kHz to 5 MHz or more. The exact frequencies, however, are variable, depending on the exact dimensions and mechanical properties of the cantilever and a variation in manufacturing of 20-50% from nominal values is not uncommon.

A variety of modulation techniques exist, including photoelastic modulators, electro-optic modulators, acousto-optic modulators, mechanical choppers, piezo electrically actuated mirrors, etc, but each of these suffer from one or more limitations. Some modulators work at a limited wavelength range thus limiting the spectroscopic range available and some techniques operate only over a limited range of modulation frequencies. Thus, successful application of Wickramasinghe's technique in the mid IR would ideally require:

A broad wavelength IR source, e.g. tunable from 2.5 to 10 um or preferably 2.5 to 16 um.

An IR modulator operable over the entire mid IR wavelength range.

The ability to tune the frequency of the IR modulator over the range of difference frequencies desired, e.g. from 250 kHz to 6 MHz or more.

The current inventors are not aware of generally applicable modulation techniques that can be tuned from 250 kHz to 6 MHz and are operable in the mid-IR from 2.5-16 um. Thus, it is the object of this invention to provide novel techniques practical in the IR to apply the heterodyne detection technique to highly localized AFM based IR spectroscopy.

BRIEF SUMMARY OF THE INVENTION

The invention is a method of obtaining nanoscale measurements of optical absorption of a sample with an oscillating cantilever probe of a probe microscope and a modulated source of infrared radiation. The invention overcomes limitations of the prior art by enabling a method that works practically in the infrared wavelengths over a wide wavelength range. To achieve this, the method includes illuminating a region of a sample with a beam source of infrared radiation, further modulating the tip-sample separation at at least two frequencies, and then modulating the IR source to create a force at a nonlinear beat frequency substantially corresponding to a resonance of the cantilever. The invention further comprises detecting an amplitude of oscillation of the cantilever at the resonance and deriving from the detected amplitude an infrared absorption spectrum of a region of the sample under the probe tip. In certain embodiments, the cantilever probe is oscillated at a frequency, $f_1$ and the probe microscope is operated in non-contact or intermittent contact mode. More specifically the AFM can be operated in attractive or repulsive oscillating tip modes. In a preferred embodiment, the modulated source is a pulsed IR laser.

In various embodiments the method includes oscillating the cantilever at a first frequency $f_1$, substantially corresponding to a frequency $f_{c1}$ of a resonant mode of the cantilever, optionally modulating the relative tip-sample distance at a second frequency $f_2$, illuminating a sample with a modulated beam of radiation with a modulation frequency $f_m$, and; selecting $f_2$ and $f_m$ such that a mixing force component occurs at a nonlinear beat frequency approximately equal to $f_{c2}$ where $f_{c2}$ is the frequency of another resonant mode of the cantilever. Possible combinations include $f_{c2}=f_2+nf_{fm}$ wherein n is an integer. Note that n can be a positive or a negative integer because the nonlinear beat frequencies occur at both sum and difference frequencies. The sample interaction with the modulated IR beam at $f_m$ results in a tip-sample force at $f_m$. Nonlinear tip-sample forces then mix the force at $f_m$ with tip-sample motion at $f_2$ resulting in an excitation of the cantilever at resonance $f_{c2}$. Note that there is no requirement that $f_2$ is greater than $f_1$ or that $fc_2$ is greater than $f_{c1}$. In one embodiment $f_{c1}$ is selected to be the $1^{st}$ flexural bending mode of the cantilever and $f_{c2}$ is selected to be the $2^{nd}$ flexural bending mode. But $f_{c1}$ may in fact be chosen to be the $2^{nd}$ flexural mode and $f_{c2}$ may be chosen to be the first flexural mode. Other combinations of first and second resonances are possible as well. The beam modulation frequency, $f_m$, is preferably at least 1 kHz.

The method may also include the step of measuring an amplitude of cantilever vibration at or around $f_{2c}$ and may also include the steps of repeating the measurement of cantilever amplitude at a plurality of wavelengths of the beam of radiation. In this case, the cantilever amplitude as a function of wavelength or wavenumber is indicative of the absorption spectrum of material interacting with the tip of the probe microscope.

In other embodiments, the peak of the cantilever oscillation at $f_{c2}$ has a half width of $F_{c2hw}$, and $f_m$ is chosen to be greater than $f_{c2hw}$, to ensure that $f_2$ will not excite a significant cantilever response at $f_{c2}$ absent sample/tip interaction at $f_m$. In further embodiments $f_{c2}/f_m$ is not equal to an integer, to avoid direct excitation of the cantilever at resonance $f_{2c}$ due to harmonics of $f_m$ being equal to $f_{c2}$. $f_m$ is preferably chosen to be a pulse rate of a pulsed IR laser low enough to result in power sufficient for the measurements.

BRIEF DESCRIPTION OF THE DRAWINGS

The invention will be better understood by referring to the following figures.

DETAILED DESCRIPTION OF THE INVENTION

Figure 1:
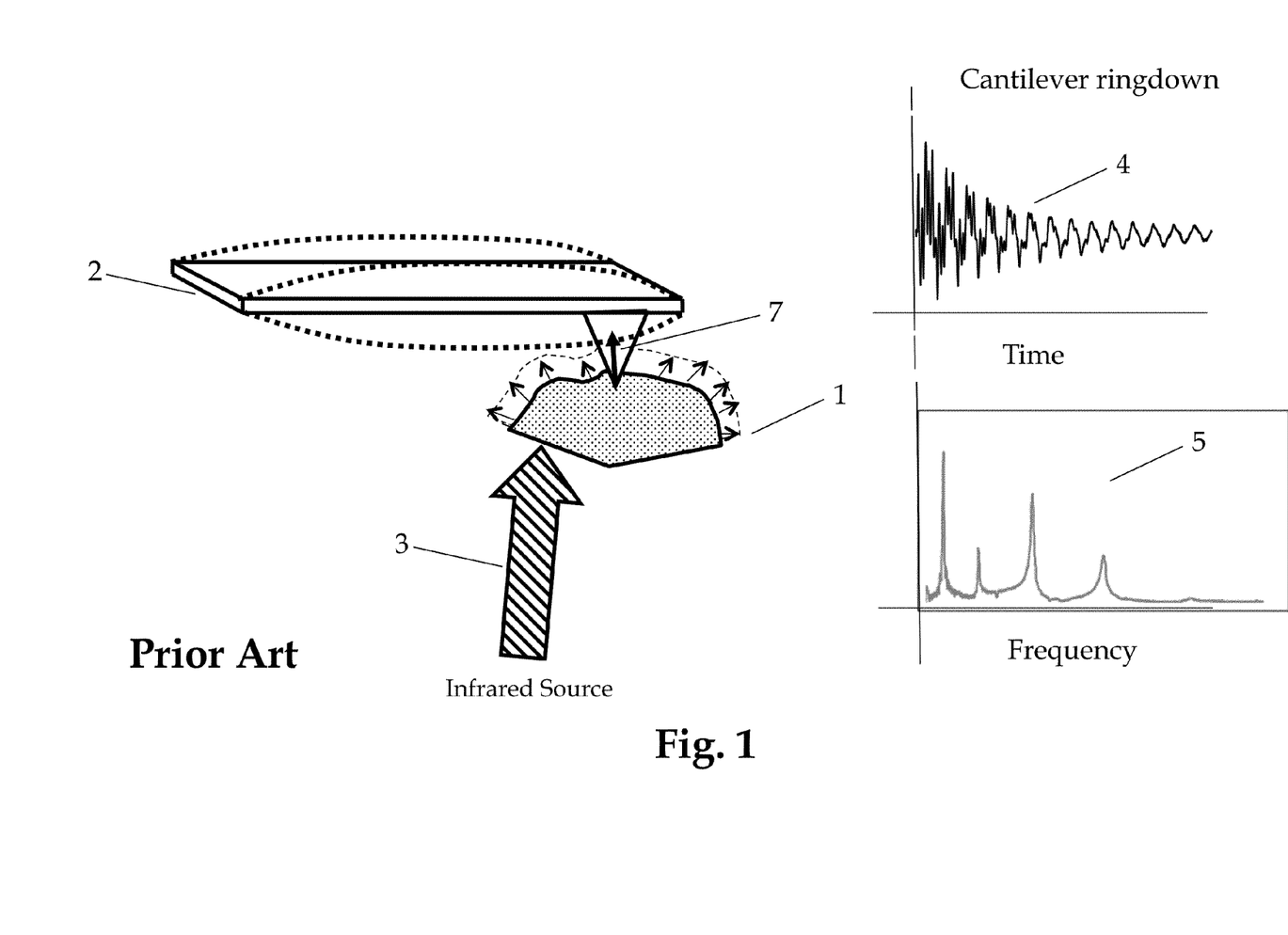
FIG. 1 is a simplified illustration of the prior art PTIR technique.

Referring to FIG. 1 the basics for a prior art PTIR system are shown. Sample 1 is probed by an AFM with a cantilever probe 2. The interaction between the probe and sample may be contact, non-contact, near contact, intermittent contact and/or tapping or other method of interaction that generates a measurable probe response as a function of the interaction. A pulsed IR beam 3 is directed at the sample 1. Adsorption of the beam will cause localized heating in the sample resulting in a thermal expansive interaction with the probe tip resulting in a decaying contact resonance ringdown 4. The characteristics of this ringdown waveform, which may be characterized by a spectrum of the waveform 5, depend on the absorption properties of the material under the tip. If the measurement is repeated at multiple source wavelengths as absorption spectra may be produced, leading to identification of the material in the immediate vicinity of the probe tip.

Figure 2:
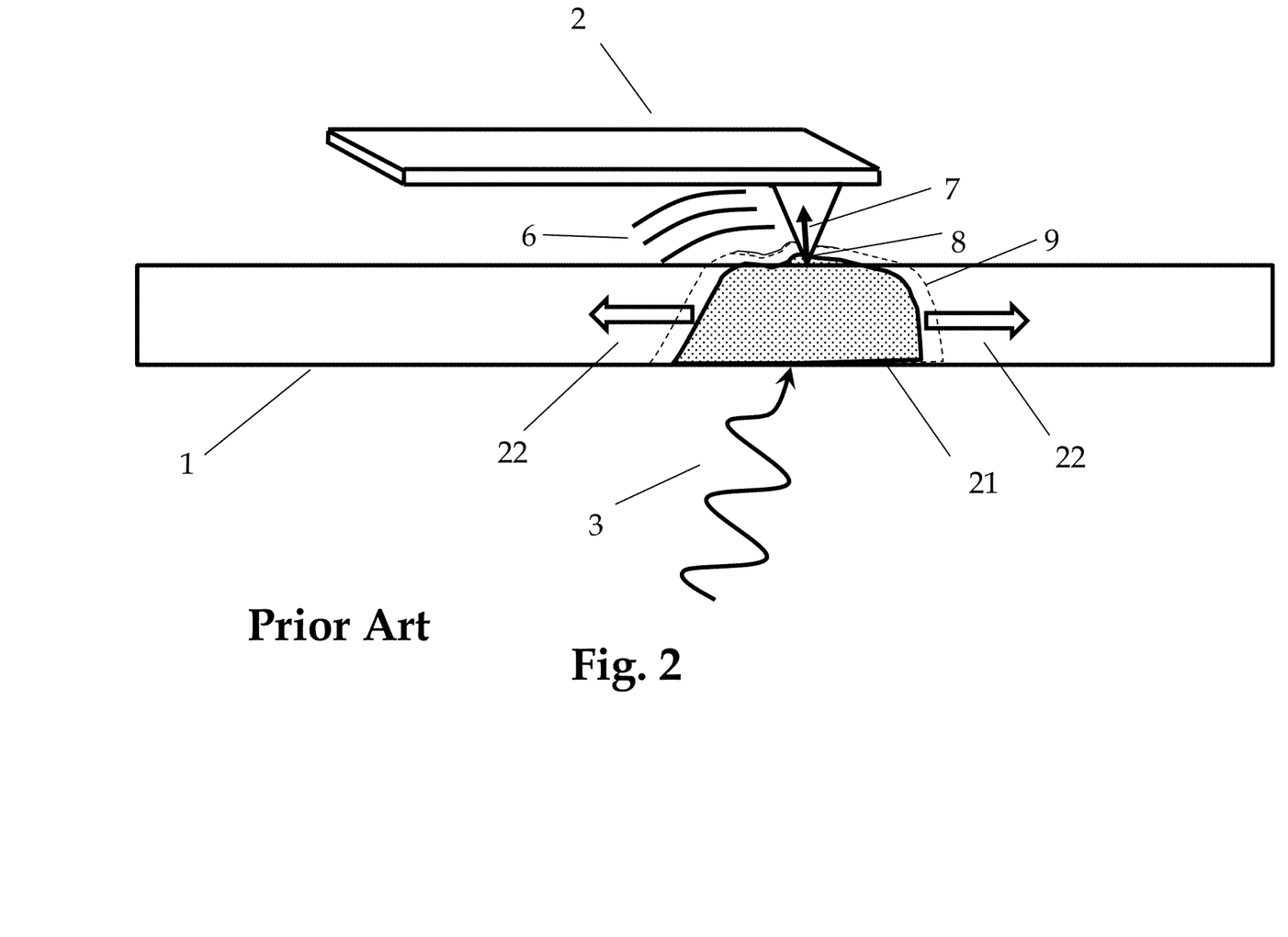
FIG. 2 is an illustration of the background effects that delocalize the measurement in prior art PTIR.

FIG. 2 illustrates that the forces interacting with the probe in conventional PTIR are not confined to the region directly under the tip. When laser pulse 3 impinges on an absorbing region 21 of sample 1, the absorbing region will rapidly heat causing thermal expansion, as indicated by exaggerated profile 9. This thermal expansion creates a force impulse 7 at the tip apex 8 of cantilever 2. The rapid heating, however, also creates other non-local forces that can negatively affect the spatial resolution of the conventional PTIR technique. For example, rapid heating of the sample can cause a pressure wave 6 to travel through the air to hit other surfaces of the cantilever including the shank of the AFM tip and the planar surfaces of the cantilever. Background absorption of light by the cantilever or its surface coatings may also exist. Conventional PTIR is also performed in contact mode AFM. Contact mode has disadvantages that can include higher tip-sample forces, higher lateral forces, degraded spatial resolution and potential tip-sample damage. Further, since the tip is in constant contact with the sample surface, the tip is susceptible to tip-sample forces that occur over an extended time after the laser pulse. This can lead to degradation of the spatial resolution due to thermal diffusion. Specifically, heat can spread from an absorbing area into a nonabsorbing area (as indicated by arrows 22) creating a detectable thermal expansion and thus cantilever ringdown on a sample region where there is no IR absorption at a given wavelength. All of these effects can contribute to the measured probe motion and thus can have a delocalizing effect on the PTIR measurement.

Figure 3:
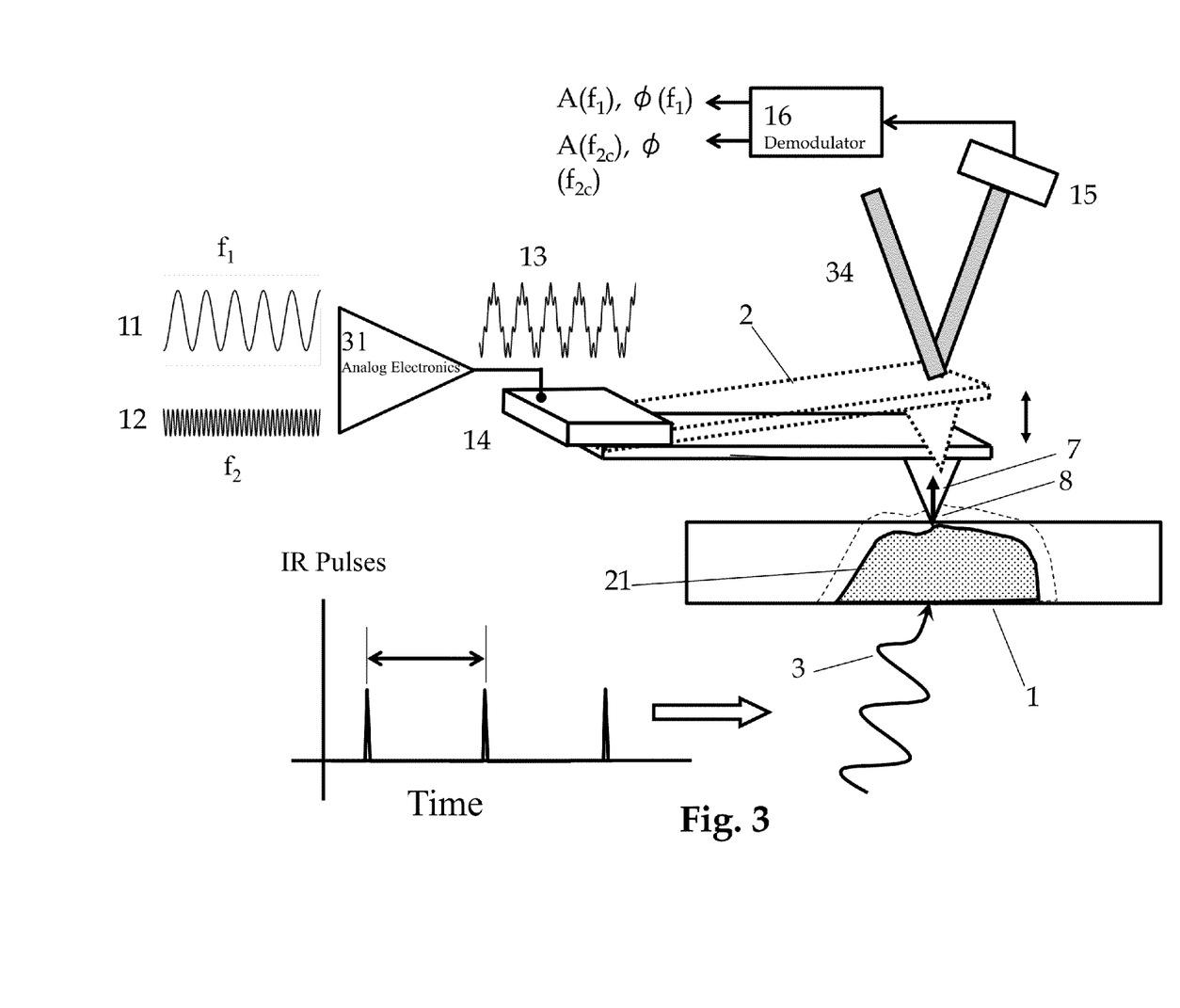
FIG. 3 is a block diagram of the elements of the invention employing multiple modulation heterodyne AFM-IR spectroscopy.

FIG. 3 shows an AFM-IR system under the current invention. In the current invention, a cantilever probe 2 is oscillated at atg least two frequencies, $f_1$ and $f_2$ as shown by waveforms 11 and 12. In one embodiment one of $f_1$ is selected to substantially correspond to one of the cantilever's resonant modes at frequency $f_{c1}$. Often the probe resonance $f_{c1}$ is selected to correspond to the cantilever's first bending mode, but this is not required. As discussed elsewhere, in some cases it can be advantageous to select a higher order oscillation mode for $f_{c1}$. It is also possible to oscillate the cantilever away from a flexural resonance or rapidly modulate the tip-sample distance (e.g as described for example in Jumping Probe Microscope (U.S. Pat. No. 5,266,801) or Pulsed Force Mode patents (e.g. U.S. Pat. No. 6,880,386.) The cantilever-sample separation is also modulated at a second frequency $f_2$, as indicated by waveform 12. This frequency $f_2$ is selected to be close to, but not exactly aligned with a second cantilever mode resonance at $f_{c2}$. The frequency $f_{c2}$ may correspond to the next higher flexural bending mode, but it can also be selected to be any higher or lower vibration mode, including flexural, lateral and torsional or compound vibration modes. Waveforms 11 and 12 can be combined into compound waveform 13 in any number of ways. They can be synthesized separately and then added or subtracted using analog electronics (schematically shown in 31), or combined with an RF mixer. Alternatively, the two signals can be generated and combined digitally such that a single multifrequency waveform 13 is sent to modulate the cantilever. The cantilever may oscillated using an actuator 14, which may be piezoelectric, thermal, electrostatic, magnetic, optical or any other mechanism that can apply a force to the cantilever and/or the cantilever mount at the desired frequencies. In the case of electrically driven actuators, for example a piezo actuator, the two drive waveforms 11 and 12 may also be applied to opposing electrodes of the piezo actuator. It is also possible to apply one of the oscillation signals to an actuator that modulates the cantilever position and the other modulation signal to an actuator that modulates the sample. In any of these multiple modulation configurations the key is that the tip-sample separation is modulated at at least two different frequencies.

Next, light 3 from a broadly tunable infrared source (not shown) is focused on a region of a sample 1 substantially aligned to a point of tip-sample interaction. In one embodiment, the IR light is delivered in pulses at a pulse repetition rate of $f_m$. In other embodiments, the light source may be a CW source that is chopped or sinusoidally modulated at rates including a component at frequency $f_m$. The motion of the cantilever is then measured using a deflection detection system and signal is demodulated to determine the component at frequency $f_2+nf_{fm}$. The most common way to measure the cantilever deflection is using the optical lever technique where a laser beam 34 is directed to the cantilever and the reflected beam is sent to a position sensitive detector 15. Many alternate techniques are employed for measuring the cantilever deflection, including interferometric, capacitive, piezoelectric, piezoresistive, and thermal sensing techniques to name a few. Once a signal indicative of the cantilever motion is obtained, it is demodulated to determine the strength of the signal at at least two key frequencies. First, the signal can be demodulated to determine the amplitude, phase, and/or frequency of the cantilevers fundamental resonance around $f_{c1}$. This signal may be used in a feedback loop to attempt to keep the average tip-sample interaction force constant. For example, in intermittent contact mode the average amplitude of the cantilever oscillation is maintained roughly constant. In some implementations of non-contact mode, the feedback loop aims to maintain the resonant frequency shift at a constant value.

In addition, the cantilever deflection signal is demodulated 16 to measure a cantilever response near a heterodyne frequency at $f_2+n*f_m$ where n is an integer. Many different techniques can be applied to demodulate this signal. For example a lock-in amplifier may be employed with a reference provided at frequency $f_2+n*f_m$. Alternately, the cantilever deflection signal can be digitally sampled and fast Fourier transform techniques can be used to extract the amplitude at $f_2+n*f_m$. A bandpass filter can be used to select the specific frequency range desired and an RMS detector can be applied to detect amplitude in the passband. A variety of other digital signal processing and/or RF demodulation techniques can be used to extract this frequency component. While it is most common to measure the amplitude A of the cantilever oscillation at this heterodyne frequency, it is also possible to measure the in phase component, $\phi$, the quadrature component, Q and/or the phase at the heterodyne frequency. Any demodulated signal that is roughly proportional to the strength of the response at this heterodyne frequency may be sufficient. Once this frequency component is available it can be used to create high resolution absorption spectra by measuring an amplitude of the cantilever deflection at $f_2+n*f_m$ versus wavelength of the infrared source. Additionally, spatially resolved absorption images can be created by measuring the amplitude of the cantilever deflection at $f_2+n*f_m$ versus position on a region of the sample.

The multiple modulation scheme described above overcomes the limitations of the prior art, especially the need to modulate the infrared source at frequencies corresponding to the higher order cantilever oscillation modes in intermittent contact/non-contact mode. The inventors realized that by employing multiple modulation frequencies and nonlinear mixing, it is possible to generate a tip-sample force at any arbitrary frequency, at much higher frequencies than the limits of modulated infrared sources. The inventors, for example have operated the multiple modulation technique with the cantilever oscillated at $f_{1c}$ of approximately 80 kHz and arranged $f_m$ and $f_2$ to create a nonlinear beat frequency at a cantilever oscillation mode at 1.9 MHz. This is well above the 50 kHz maximum repetition rate of the IR laser used in these experiments.

Figure 7:
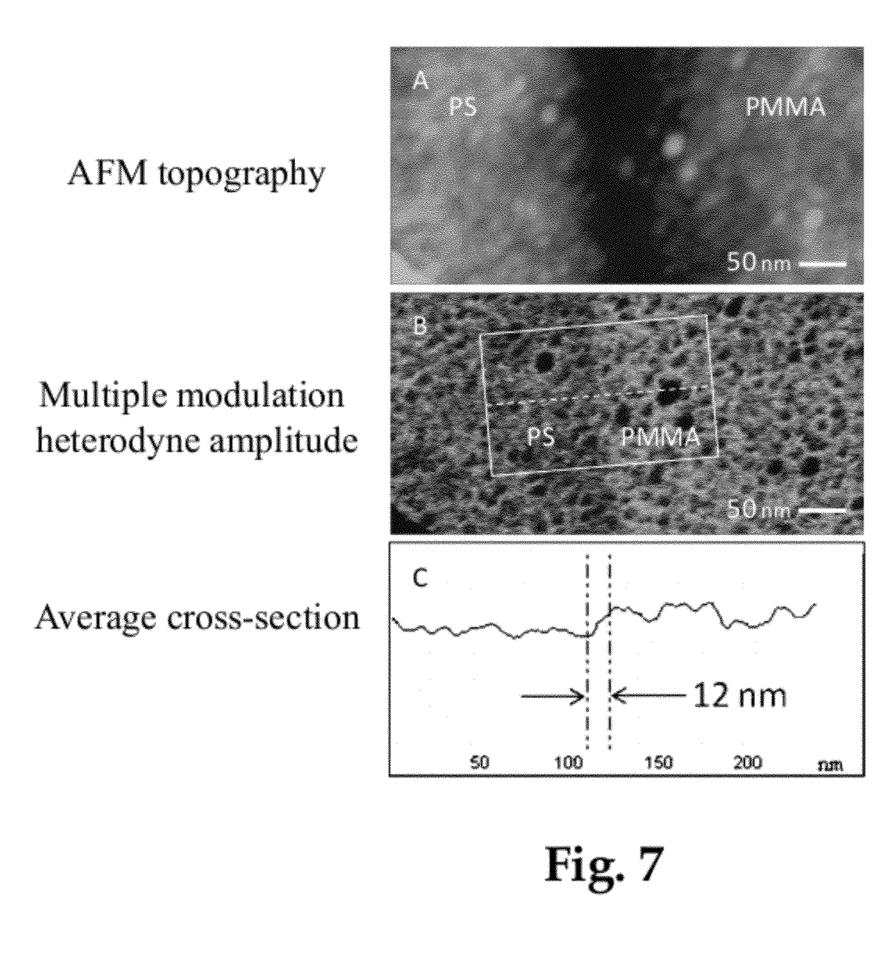
FIG. 7 shows a high resolution image obtained from a set-up using the invention.

The nonlinear mixing also overcomes some of the spatial resolution limits of the conventional PTIR technique. As described above the conventional PTIR technique has limited spatial resolution due to non-local sources of forces felt by the cantilever. In the current invention, the heterodyne force component at frequency $f_2+n*f_m$ appears only in the presence of a nonlinear tip-sample interaction. This nonlinear force is negligible when the tip is away from the surface and small when the tip is in constant contact with the sample. The nonlinear interaction is strongest only during a very brief time when the oscillating tip transitions from no interaction to contact or near contact. Thus, when the cantilever oscillation is measured at frequency $f_2+n*f_m$ it is only sensitive to near-field tip-sample forces and highly attenuates nonlocal forces from the sources described above. This has enabled the improvement of spatial resolution from the scale of 100s of nanometers to around 10 nm as illustrated in FIG. 7. Thus, at least one (more than one would work, as well) additional modulation $f_2$ is applied to the tip-sample separation. A straightforward way to do this is to simply add an $f_2$ waveform to probe oscillation driver 14, as shown in FIG. 3. However, any other tip-sample modulation, such as oscillating the sample would also be acceptable. Since electrical stimulation of small mechanical elements, such as typical AFM probes, may easily be done at the hundreds of kHz required, this additional modulation can be used to bridge the gap between attainable values of $f_m$ and a higher resonance $f_{c2}$.

Figure 4:
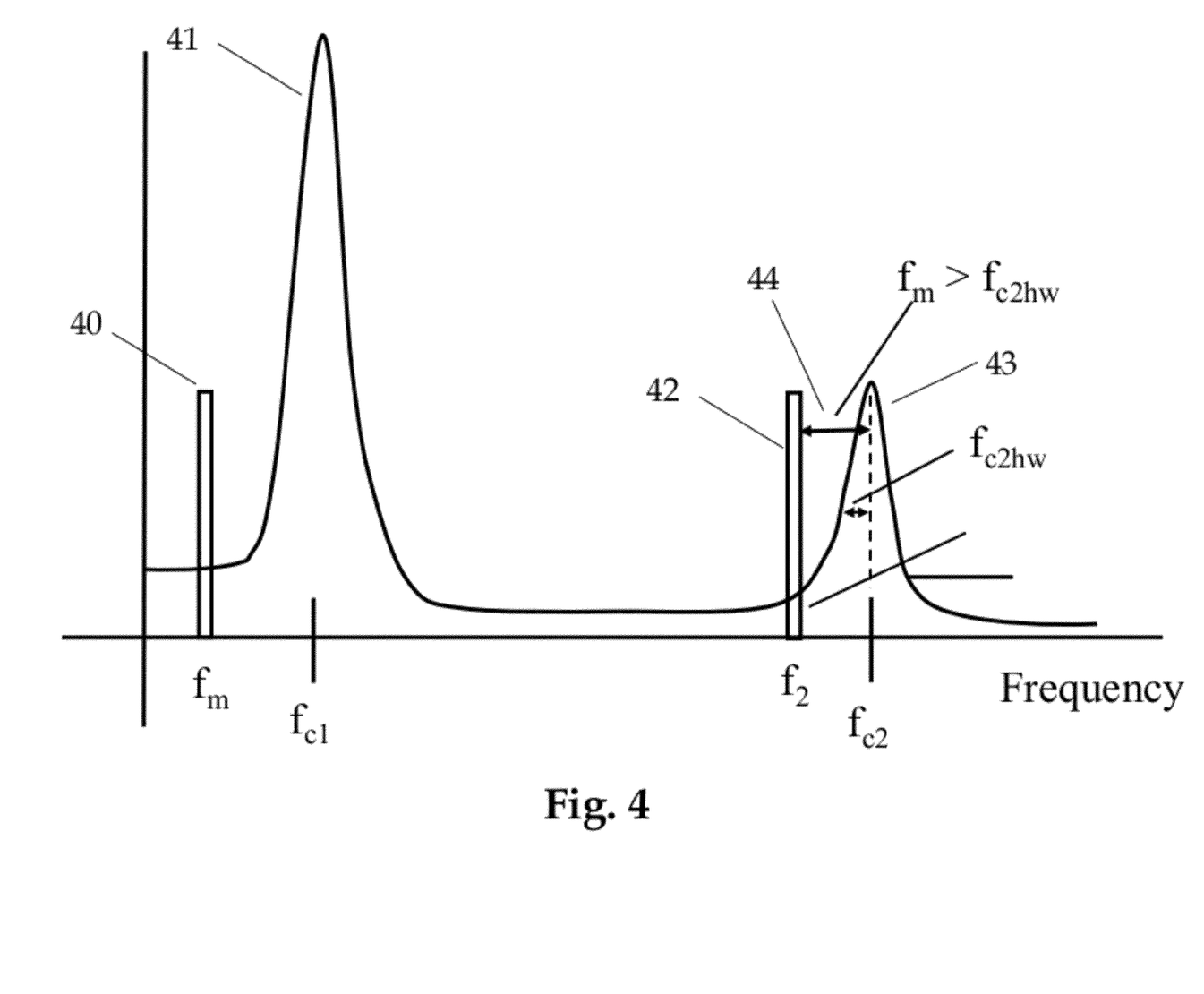
FIG. 4 shows the non-linear mixing scheme of the current invention.

Thus, the operation of the invention is shown in FIG. 4. In one embodiment, the probe is oscillated at a first probe resonance peak 41 at $f_{c1}$, which is shown along with another probe resonance $f_{c2}$ 43. Although these may be the first and second cantilever flexural modes, it is not required that they be; and in fact the invention may operate at any two oscillation modes with sufficient sensitivity. (It is also possible in some cases to operate off one or more of the resonant peaks.) A second modulation 42 of the tip-sample distance $f_2$ is also applied. The IR source is modulated at $f_m$ as indicated schematically by the band 40. The frequencies $f_m$ and $f_2$ are chosen such that they substantially satisfy this relationship:

$$f_{c2}=f_2+nf_m$$

where n is an integer. In the case that the IR source is pulsed at a repetition rate of $f_m$, higher harmonics of $f_m$ (i.e. at frequencies of $nf_m$) have large amplitudes so that is why many harmonics of $f_m$ are usable and the reason for the term n in the equation. So $f_2$ can be easily chosen high enough to allow for an achievable value for $f_m$. The case n=1 is shown in FIG. 4. In this case the difference frequency 44 between $f_2$ and $f_{c2}$ is equal to the laser modulation frequency $f_m$.

For example if $f_{c1}$ is 80 kHz, a value consistent with commercial AFM probes, $f_{c2}$ may be around 480 kHz. A reasonable value for the modulation frequency achievable for a broad band IR source is ~10 kHz. Thus $f_2$ could be chosen to be 470 kHz or 490 kHz, an easily achievable mechanical oscillation for an AFM probe or a small sample.

There is a subtle detail in the optimal selection of $f_m$. It is generally desirable that $f_2$ is selected sufficiently off resonance from $f_{2c}$ so as not to excite appreciable amplitude in the absence of the nonlinear tip-sample interaction. Thus, as shown in FIG. 4 it is desirable that $f_m$ be chosen such that:

$$f_m > f_{c2hw}$$

Where $f_{2chw}$ is the halfwidth of the resonance peak 43. This will ensure that the excitation at $f_2$ doesn't excite an excessive amplitude within the resonance peak 43 centered on $f_{c2}$. In the case of a pulsed IR source, the selection of pulse repetition rate $f_m$ may also be influenced by frequencies at which the pulse energy begins to drop off. For example, in one source used in these experiments, while the pulse rate available was as high as 50 kHz, lower repetition rates (e.g. 10 kHz) were selected to maintain higher pulse energies.

Additionally, if $f_m$ is selected to be an arbitrary frequency, there is a chance that a harmonic of $f_m$ may overlap the second resonance peak and excite it even for the case where there is no nonlinear tip-sample interaction to the IR beam. The reason is that the non-local forces described in paragraph 13 resulting from the rapid sample heating have force components at $f_m$, $2f_m$, $3f_m$, etc. Thus it is possible to excite the cantilever at $f_{c2}$ in the case that $f_{c2} \approx nf_{fm}$ just due to the non-local forces. Since a goal of this invention is to improve the spatial resolution of AFM-based IR spectroscopy, the inventors have sought to substantially attenuate sensitivity to these background forces high resolution measurements. To achieve this, it is desirable to select $f_m$ such that no harmonics of $f_m$ fall within the envelope of the resonance curve of $f_{c2}$. Specifically, this means that $f_m$ should ideally be selected such that:
$f_{c2}-f_{c2hw}<nf_{fm}<f_{c2}+f_{c2hw}$ for the value of n that gives $nf_{fm}$ closest to $f_{c2}$.

The value of $f_m$ is generally selected in an iterative manner. First a rough value $f_{m,start}$ is selected such that $f_{m,start}>f_{c2hw}$ as described above. Then a fine adjustment is made to the value of $f_m$ to center $nf_{fm}$ and $(n+1)f_{fm}$ roughly equally separated from $f_{c2}$. Specifically, the final value of $f_m$ may be selected according to:

$$f_{m,final}=f_{c2}/(INT(f_{c2}/f_{m,start})^{1/2})$$

Figure 5:
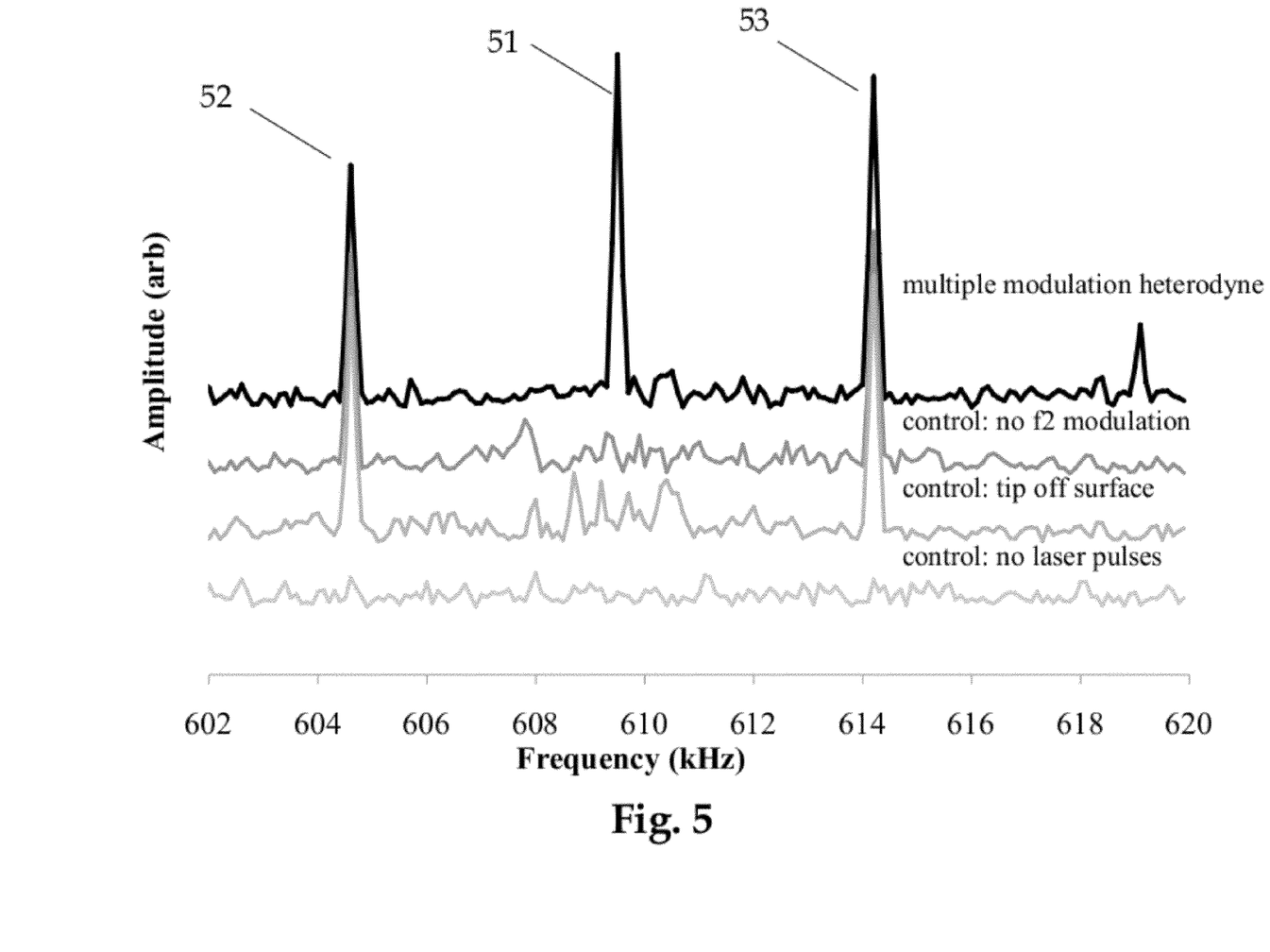
FIG. 5 shows a series of Fourier transforms of the cantilever deflection signal obtained using the current inventions.

For example if $f_{m,start}$ is selected to be 10 kHz, and $f_{c2}$ is 480 kHz, the equation above will suggest a refined value of $f_{m,final}=9.897$ kHz, a frequency such that the $48^{th}$ and $49^{th}$ harmonics of the modulation frequency at 475.052 kHz and 484948 kHz are equally separated from $f_{c2}$ by $f_{m,final}/2=4.948$ kHz. Example measurements showing appropriate selection of $f_m$ to avoid harmonics overlapping the cantilever resonance is shown in FIG. 5.

Thus with the above improvement, data is taken at $f_{c2}$, and the data varies with source wavelength. So the data does still correlate with a spectra as in a PTIR setup, albeit at improved spatial resolution.

In an alternate embodiment it is possible to modulate the tip-sample separation with a single actuator at a single frequency $f_1$. In this configuration the cantilever can be oscillated at a frequency $f_1$ close to but not centered on a cantilever resonant frequency $f_{c1}$. More specifically, the cantilever will be oscillated at $f_{c1}-f_m$ where $f_m$ is a modulation frequency of the IR source. The drive frequency $f_1$ may be selected such that $f_1$ is on the shoulder of the resonance curve at $f_{c1}$. (Driving off resonance can have other benefits, including faster response of the cantilever to transient tip-sample forces encountered as the tip scans over a sample surface.) Then the laser modulation frequency $f_m$ may be selected such than $f_1+n*f_m$ is equal to $f_{1c}$. For example, a cantilever with a first free flexural resonance at 70 kHz can be driven at around 60 kHz and the laser can be modulated at 10 kHz. The drive at 60 kHz can produce sufficient oscillation amplitude to allow intermittent contact or noncontact operation, but the heterodyne force at 60 kHz+10 kHz=70 kHz will be amplified by the cantilevers resonant properties at $f_{c1}$.

The infrared source can be any number of sources, for example those discussed in U.S. Pat. Nos. 8,001,830, 8,646,319, 8,402,819, and 8,242,448, which are included by reference. AFM-based infrared spectroscopy has been demonstrated, for example, using lasers based on optical parametric oscillators, quantum cascade lasers, globar sources using commercial Fourier Transform Infared Spectrometers, and a free electron laser. More recently Raschke et al have demonstrated the use of a heated AFM cantilever as a local source of broadband IR radiation. Other sources such as comb drive devices may also be suitable. Any of these sources and other infrared sources may be used individually or in combination as long as the source can be modulated or pulsed at a frequency on the scale of a few kHz or higher. As mentioned previously, there are many techniques for modulating the output of the IR source. The modulation can be achieved by the IR source itself (e.g. pulsed sources) or through external modulation technologies, some examples described in paragraph 6. The phrase "modulating the IR source" should be understood to mean modulating the output energy of the IR source by internal and/or external means. In a preferred embodiment, the IR source is a multistage optical parametric oscillator tunable from 2.5 um to 10 um or more preferably from 2.5 to 16 um. Technology for creating such a laser is described in the previously mentioned copending applications. It is also possible to use broadband IR sources, such as globars, and Fourier transform techniques to determine the wavelength dependence of the IR absorption.

Figure 6:
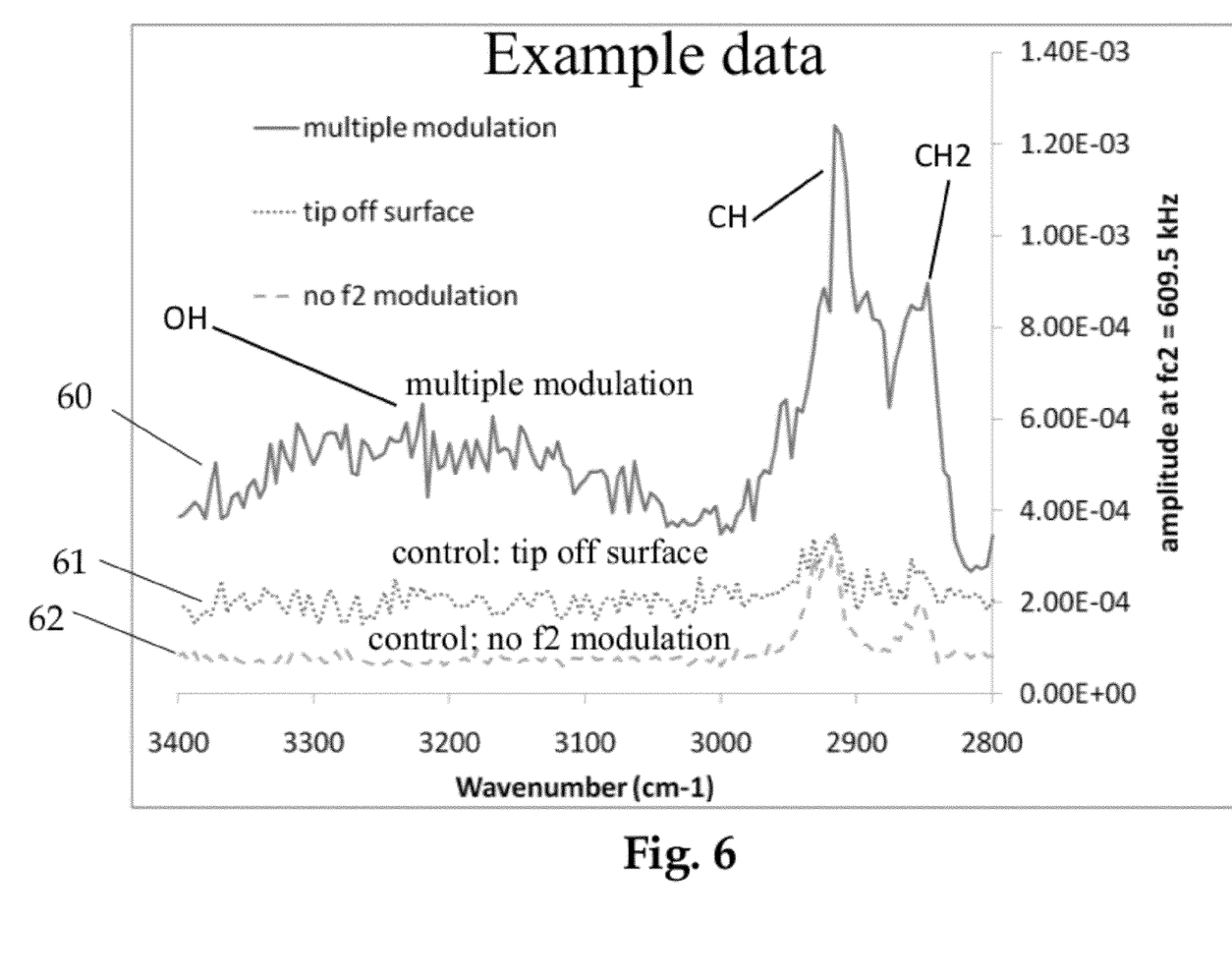
FIG. 6 shows infrared spectra obtained from a set-up utilizing the invention.

Example measurement results using the multiple modulation heterodyne technique are shown in FIGS. 5-7. FIG. 5 shows a series of Fourier transforms of the cantilever deflection signal taken with the multiple modulation heterodyne technique versus various control experiments. The dark curve on top shows a peak 51 at around 609.5 kHz corresponding to the nonlinear mixing of $f_2$ around 599.6 kHz and $f_m$ around 9.9 kHz. Note that peak 51 is only present in the multiple modulation heterodyne case. Peaks 52 and 53 correspond to the $61^{st}$ and $62^{nd}$ harmonic of the pulse repetition rate of $f_m$=9.9 kHz. Note that $f_m$ has been selected such that these harmonics are well separated from the cantilever's $2^{nd}$ resonance peak 51 at 609.5 kHz.

FIG. 6 shows an example spectrum taken on a commercial polyethylene/polypropylene polymer film along with some control experiments taken in the same location. THIS measurement was performed with top-surface illumination by the IR source in intermittent contact mode without any special sample preparation. The top curve 60 show a multiple modulation heterodyne absorption spectrum. Trace 61 was taken when the tip was lifted very slightly out of the intermittent contact regime, but with the multiple modulation drive signals still present along with the IR source focused on the sample. Trace 62 has the tip back in intermittent contact mode, but the amplitude of the $f_2$ modulation was set to zero. The trace 60 obtained in multiple modulation heterodyne mode is certainly noisier than some traditional PTIR spectra, but this is due to sampling the IR absorption over a much smaller spatial volume. The spectrum in 60 shows CH and CH2 stretch bands expected for the polymer film but is also striking in that it shows a broad absorption around 3250 cm-1, very likely due to the OH absorption of nanometer scale layers of adsorbed water. To our knowledge, this level of surface sensitivity has never been observed with traditional AFM-IR measurements.

FIG. 7 shows an example of spatially resolved measurements performed with the multiple modulation heterodyne technique. The sample measured was a blend of polystyrene (PS) and polymethylmethacrylate (PMMA). These measurements were performed at the interface between the two materials. The top image (A) shows a measurement of AFM topography across the interface. The center image (B) is a measurement of the amplitude of the cantilever oscillation at $f_{c2}$ using the multiple modulation technique. The cross-section in panel C represents the average cross-section across the interface between PS and PMMA over the region indicated by the white rectangle in (B) and in the direction indicated by the dashed line. Note that there is a clear amplitude difference between the PS and PMMA in the multiple modulation image (B). The transition distance between the height levels is of order 12 nm as indicated by the arrows. This demonstrates the ability to spatial resolve chemical differences on scales much smaller than conventional PTIR. Note also that there is clear contrast within the PS and PMMA regions. This contrast is associated with variations in the surface topography which can serve to concentrate the forces felt by the AFM tip. There may be multiple sources for this topographic artifact, but one includes the fact that the electric field between the AFM tip and the surface depends on dC/dz, the derivative of the tip-surface capacitance in the vertical direction. This term is dependent on the relative sharpness of surface asperities. To decouple these effects it is possible to obtain multiple modulation heterodyne images at multiple wavelengths. While the IR absorption is of course wavelength dependent, the capacitance term dC/dz is not. So measurements at multiple wavelengths can be used to normalize for this and other effects. It is also possible to use the AFM topography measurement to calculate the local value of dC/dz and multiple modulation heterodyne images can then be scaled by the calculated dC/dz values at each point.

It will be apparent to the skilled artisan that there are numerous changes that may be made in embodiments described herein without departing from the spirit and scope of the invention. Other features not mentioned in the specification, but known to one skilled in the art may be integrated as well without departing from the spirit and scope of the present invention. There are, for example, a wide array of materials, apparatuses, and methods which may be interchangeably used, and there are many changes that may be made in dimensions and so forth to accommodate different needs which may be used, all within the scope of the invention. The methods, system, and apparatuses of the present invention should therefore be afforded the broadest possible scope under examination. As such, the invention taught herein by specific examples is limited only by the scope of the claims that follow.

We claim:

1. A method of obtaining nanoscale measurements of optical absorption of a sample with an oscillating cantilever probe of a probe microscope and a source of infrared radiation, the method comprising:

modulating the infrared source at a frequency $f_m$;
illuminating a region of a sample with a beam from the modulated, infrared source of infrared radiation; oscillating the cantilever at a first frequency $f_1$;
modulating the tip-sample separation at at least one second frequency $f_2$; and, detecting an oscillation of the cantilever at a frequency $f_2+nf_m$, where n in an integer.

2. The method of claim 1 further comprising the step of deriving an infrared absorption spectrum for a region of the sample under the probe tip from the detected oscillation at a frequency $f_2+nf_m$.

3. The method of claim 2 wherein a detected amplitude is measured with a spatial resolution of less than 100 nm.

4. The method of claim 1 further comprising the step of measuring the detected amplitude at a plurality of locations on the sample surface to create an image indicative of infrared absorption across a region of the sample.

5. The method of claim 4 further comprising the step of correcting the absorption imaged based on a measurement of surface topography of the region of the sample.

6. The method of claim 4 further comprising the step of correcting the absorption imaged based on measurements of a signal proportional to dC/dZ at a plurality of locations on the sample.

7. The method of claim 4 wherein the IR absorption image has a spatial resolution of better than 20 nm.

8. The method of claim 4 wherein the detected amplitude is measured with a spatial resolution of less than 100 nm.

9. The method of claim 1 wherein the frequency $f_1$ substantially corresponds to a flexural resonance of the cantilever and the probe microscope is operated in intermittent contact mode.

10. The method of claim 1 wherein the frequency $f_1$ substantially corresponds to a flexural resonance of the cantilever and the probe microscope is operated in non-contact mode.

11. The method of claim 1 wherein the modulated source is a pulsed IR laser.

12. The method of claim 1 wherein the beam modulation frequency, $f_m$, is at least 1 kHz.

13. The method of claim 1 wherein the frequency $f_2+nf_m$ is greater than 50 kHz.

14. A method of obtaining nanoscale measurements of optical absorption of a sample with an oscillating cantilever probe of a probe microscope and a source of infrared radiation, the method comprising:
 oscillating the cantilever at a first frequency $f_1$, substantially corresponding to a frequency $f_{c1}$ of a resonant mode of the cantilever;
 modulating the relative tip-sample distance at a at least one second frequency $f_2$;
 illuminating a sample with a modulated beam of radiation with a modulation frequency $f_m$; and,
 selecting $f_2$ and $f_m$ such that combinations including ($f_2+nf_m$) are approximately equal to $f_{c2}$, where $f_{c2}$ is the frequency of another resonant mode of the cantilever, and where n is an integer.

15. The method of claim 14 wherein sample interaction with the modulated beam at $f_m$ results in a probe response at $f_m$ resulting in an excitation of the cantilever at resonance $f_{c2}$.

16. The method of claim 14 further comprising the step of measuring an amplitude of cantilever vibration at or around $f_{2c}$.

17. The method of claim 16 further comprising the step of repeating the measurement of cantilever amplitude at a plurality of wavelengths of the beam of radiation.

18. The method of claim 17 wherein the cantilever amplitude as a function of wavelength or wavenumber is indicative of the absorption spectrum of material interacting with the tip of the probe microscope.

19. The method of claim 14, wherein the resonant peak of the cantilever oscillation at $f_{c2}$ has a half width of $F_{c2hw}$, and $f_m$ is chosen to be greater than $f_{c2hw}$, to ensure that $f_2$ will not excite a significant cantilever response at $f_{c2}$ absent sample/tip interaction at $f_m$.

20. The method of claim 14 wherein $f_{c2}/f_m$ is not equal to an integer, to avoid direct excitation of the cantilever by harmonics of $f_m$ at resonance $f_{2c}$.

21. A method of obtaining nanoscale measurements of optical absorption of a sample with an oscillating cantilever probe of a probe microscope and a source of infrared radiation, the method comprising:
 modulating the infrared source at a frequency $f_m$;
 illuminating a region of a sample with a beam from the modulated, infrared source of infrared radiation; and,
 modulating the tip-sample separation at at least one frequency $f_1$ not centered on a cantilever resonance;
 detecting an oscillation of the cantilever at a frequency $f_1+nf_m \sim f_{c1}$ where n is an integer.

\* \* \* \* \*